(12) United States Patent
Nord et al.

(10) Patent No.: US 10,279,197 B2
(45) Date of Patent: May 7, 2019

(54) METHOD AND APPARATUS PERTAINING TO RADIATION-TREATMENT PLAN OPTIMIZATION

(71) Applicant: Varian Medical Systems International AG, Cham (CH)

(72) Inventors: Janne I. Nord, Espoo (FI); Jarkko Y. Peltola, Tuusula (FI); Juha Kauppinen, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 317 days.

(21) Appl. No.: 15/085,494

(22) Filed: Mar. 30, 2016

(65) Prior Publication Data
US 2017/0281971 A1    Oct. 5, 2017

(51) Int. Cl.
*A61N 5/00* (2006.01)
*A61N 5/10* (2006.01)
*G06F 19/00* (2018.01)

(52) U.S. Cl.
CPC ......... *A61N 5/1038* (2013.01); *A61N 5/1031* (2013.01); *A61N 5/1039* (2013.01); *A61N 5/1045* (2013.01); *G06F 19/00* (2013.01); *G06F 19/3481* (2013.01)

(58) Field of Classification Search
CPC .. A61N 5/1049; A61N 5/1031; A61N 5/1067; A61N 2005/1019; A61N 5/103
See application file for complete search history.

(56) References Cited

U.S. PATENT DOCUMENTS

| 6,038,284 | A | * | 3/2000 | Hernandez-Guerra .................... A61N 5/1048 378/108 |
| 2009/0110145 | A1 | | 4/2009 | Lu et al. |
| 2010/0054410 | A1 | * | 3/2010 | Nord .................... A61N 5/1031 378/65 |
| 2010/0177871 | A1 | | 7/2010 | Nord et al. |
| 2013/0204067 | A1 | | 8/2013 | Nord et al. |
| 2015/0141733 | A1 | | 5/2015 | Kumar et al. |

FOREIGN PATENT DOCUMENTS

EP    2808057 A1    12/2014

OTHER PUBLICATIONS

Invitation to Pay Additional Fees from International Application No. PCT/EP2017/057046 dated May 17, 2017; 11 pages.

* cited by examiner

Primary Examiner — Don Wong
(74) *Attorney, Agent, or Firm* — Fitch, Even, Tabin & Flannery LLP

(57) ABSTRACT

A radiation-treatment plan that comprises a plurality of dose-delivery fractions can be optimized by using fraction dose objectives and at least one other, different dose objective. This use of fraction dose objectives can comprise accumulating doses delivered in previous dose-delivery fractions. The other, different dose objective can comprise a remaining total dose objective, a predictive dose objective, or some other dose objective of choice. An existing radiation-treatment plan having a corresponding resultant quality and that is defined, at least in part, by at least one delivery parameter can be re-optimized by specifying at least one constraint as regards that delivery parameter as a function, at least in part, of that resultant quality and then applying that constraint when re-optimizing the existing radiation-treatment plan.

6 Claims, 2 Drawing Sheets

METHOD AND APPARATUS PERTAINING TO RADIATION-TREATMENT PLAN OPTIMIZATION

TECHNICAL FIELD

This invention relates generally to the optimization of radiation-therapy treatment plans.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient. For example, many treatment plans comprise a series of delivery fractions that provide for exposing the target volume to possibly varying dosages of radiation from a number of different directions. Arc therapy, for example, comprises one such approach.

Such treatment plans are often optimized prior to use. (As used herein, "optimization" will be understood to refer to improving a candidate treatment plan without necessarily ensuring that the optimized result is, in fact, the singular best solution.) Though important to the use of treatment plans, typical optimization processes are computationally intensive. This, in turn, can require the use of expensive processing platforms and/or a considerable amount of processing time. Such burdens, however, can lead to unwanted costs and/or delay for the service provider and/or the patient.

Existing approaches in these regards, while useful, are not necessarily best suited for all potential application settings.

BRIEF DESCRIPTION OF THE DRAWINGS

The above needs are at least partially met through provision of the method and apparatus pertaining to radiation-treatment plan optimization described in the following detailed description, particularly when studied in conjunction with the drawings, wherein.

Figure 1:
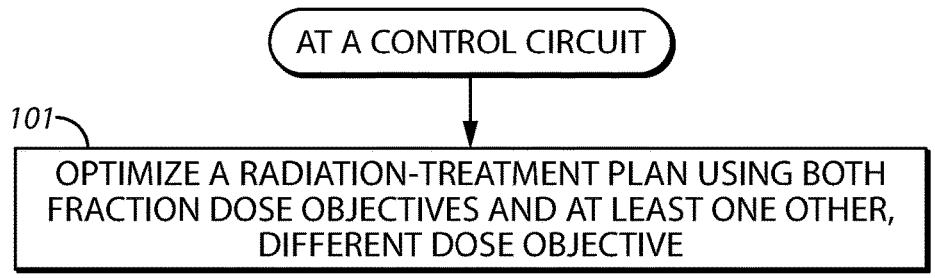
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various ones of these embodiments, a radiation-treatment plan that comprises a plurality of dose-delivery fractions is optimized, at least in part, by optimizing that plan using fraction dose objectives and at least one other, different dose objective. By one approach, this use of fraction dose objectives can comprise, at least in part, accumulating doses delivered in previous dose-delivery fractions. By one approach, such accumulation can comprise producing a mapping from fraction geometry to reference geometry and then using that mapping to accumulate the doses in the reference geometry. By another approach, the aforementioned fraction dose objectives can comprise, at least in part, dose-volume histogram objectives. The other, different dose objective can comprise, for example, a remaining total dose objective, a predictive dose objective, or some other dose objective of choice.

Also pursuant to various ones of these embodiments, an existing radiation-treatment plan having a corresponding resultant quality and that is defined, at least in part, by at least one delivery parameter can be re-optimized by specifying at least one constraint as regards that delivery parameter as a function, at least in part, of that resultant quality and then applying that constraint when re-optimizing the existing radiation-treatment plan. Using this approach can serve to at least substantially maintain the resultant quality of the re-optimized plan while nevertheless permitting changes to the existing radiation-treatment plan.

In such a case, and as one example in these regards, the aforementioned delivery parameter can pertain to fluence. By another approach, in lieu of the foregoing or in combination therewith, the aforementioned delivery parameter can pertain to one or more mechanical settings of the corresponding radiation-delivery apparatus. This can comprise, for example, mechanical settings as regards multi-leaf collimator leaf position settings. Other examples include, but are not limited to, collimator angle and/or position, patient support positions/movement, and dose-administration rates.

So configured, radiation-treatment optimization plans can be formed and/or re-optimized in ways that can yield, at least under some operating circumstances, superior results and/or useful results that require less processing time and/or computational capacity as compared to other approaches in these regards. These teachings are readily applied in conjunction with existing radiation-treatment platforms and can serve to leverage the continued utility of those platforms. These approaches are also highly scalable and can be employed to good purpose in a wide variety of application settings and for any number of differing radiation-treatment modalities and methodologies.

These and other benefits may become clearer upon making a thorough review and study of the following detailed description. Referring now to the drawings, and in particular to FIG. 1, an illustrative process 100 that is compatible with many of these teachings will now be presented. This process 100 can be carried out by an appropriately configured control circuit as described below.

This process 100 can be applied when optimizing a radiation-treatment plan comprised of a plurality of dose-delivery fractions. Many radiation treatments are parsed into treatment fractions to accommodate the fact that, for example, patient geometry may change over the course of treatment (as, for example, the position of the radiation source relative to the patient changes during the treatment session and/or between treatment sessions). By way of illustration, the size, shape, or position of a tumor to be treated or nearby critical organs may change.

A dose-delivery fraction comprises the treatment-parameter settings that are utilized during a fractional portion of a given treatment session. Examples include, but are not limited to, settings regarding the patient's position, the position of the radiation source with respect to the patient, dose intensity and/duration, collimator position, orientation, and configuration, and so forth.

This process 100 provides, in part, for the step 101 of optimizing such a radiation-treatment plan using both fraction dose objectives as well as at least one other different dose objective.

This can comprise, for example, limiting dose distribution for each organ/structure within a single fraction to no more than some maximum amount. By way of illustration, this can comprise specifying that the patient's spine should not receive more than a specified amount of radiation in any fraction regardless of how much radiation is received in another delivery fraction. Such a fractional-based limit can reflect a concern that a given organ/structure may not be able to satisfactorily recover from an excessive fractional dose even when the total treatment dosage is less than some other maximum value.

As another illustrative example, this can comprise ensuring at least a minimal dosage during any given delivery fraction in order to better ensure a desired biological response.

This process 100 will accommodate a variety of practices in these regards as regards the use of fraction dose objectives. By one approach, for example, this can comprise accumulating doses delivered in previous dose-delivery fractions. This can comprise, by way of example and without intending any limitations in these regards, for producing a mapping from fraction geometry to reference geometry and then using that mapping to accumulate doses in the reference geometry. This reference geometry can refer, for example, to a pre-treatment computed tomography (CT) image of the patient. Generally speaking the reference geometry can refer to any patient image (or images) that clearly represents the organs/volumes of interest. Images acquired during treatment may offer less coverage or clarity than such a reference image, but in some cases may be sufficient to support modeling the radiation dose distribution for, say, a particular subset of treatment fractions. If desired, producing this mapping can comprise, for example, determining a deformable image registration between a patient image and a reference patient image.

As another illustrative example, the fraction dose objectives can comprise, at least in part, dose-volume histogram (DVH) objectives. DVH's typical represent three-dimensional dose distributions in a graphical two-dimensional format (the three-dimensional dose distributions being created, for example, in a computerized radiation-treatment planning system based on a three-dimensional reconstruction of an X-ray computed tomography scan and study. The "volume" referred to in DVH analysis can be, for example, the radiation-treatment target, a healthy organ located near such a target, an arbitrary structure, and so forth.

DVH's are often visualized in either of two ways: as differential DVH's or as cumulative DVH's. With differential DVH's column height for a given dose bin corresponds to the volume of the structure that receives that dose. Bin doses typically extend along the horizontal axis while structure volumes (either percent or absolute volumes) extend along the vertical axis.

A cumulative DVH is typically plotted with bin doses along the horizontal axis but has a column height for the first bin that represents the volume of structure(s) that receive greater than or equal to that dose. The column height of the second bin then represents the volume of structure(s) that receive greater than or equal to that dose, and so forth. With high granularity a cumulative DVH often appears as a smooth line graph. For many application settings cumulative DVH's are preferred over differential DVH's but this process 100 can accommodate either approach.

As specified above, this step 101 provides for optimizing a radiation-treatment plan using both fraction dose objectives as well as at least one other different dose objective. This other, different dose objective can vary with the needs of a given application setting. As one useful example in these regards, this other, different dose objective can comprise a remaining total-dose objective. This comprises, for a given delivery fraction as comprises a part of a given radiation-treatment plan being optimized, some objective total-dose goal or limit less accumulated doses administered by earlier delivery fractions. This can be represented as:

$$TD_R(n) = TD_G - (FD(1) + \ldots + FD(n-1))$$

where $TD_R(n)$ refers to the total dose remaining when considering the nth fractional dose, $TD_G$ refers to the total dose goal, and FD refers to each fractional dose (with FD(1) representing the fractional dose associated with a first fractional delivery, and FD(n-1) representing the fractional dose associated with the fractional delivery just prior to the nth fractional dose.

As another useful example in these regards, this other, different dose objective can comprise, at least in part, a predictive-dose objective. This objective represents a prediction for one or more individual delivery fractions and/or an aggregation of one or more such delivery fractions. As another useful example in these regards, this other, different dose objective can comprise, at least in part, a predictive-dose objective. This objective represents a prediction for one or more individual delivery fractions and/or an aggregation of one or more such delivery fractions. By way of illustration, a total dose limit for the patient's spinal cord may be 40 Gy and the patient's spinal cord may already have received 30 Gy's during the first ten fractions of a twenty-fraction treatment. These numbers could be used to calculate that the patient is receiving 3 Gy per fraction. At this rate, the patient's spinal cord will receive a predicted total of 60 Gy during the complete treatment session and this will exceed the 40 Gy limit. In such a case this process can respond by working to minimize further dosing of the spinal cord (for example, by limiting future fractions to no more than 1 Gy).

Figure 2:
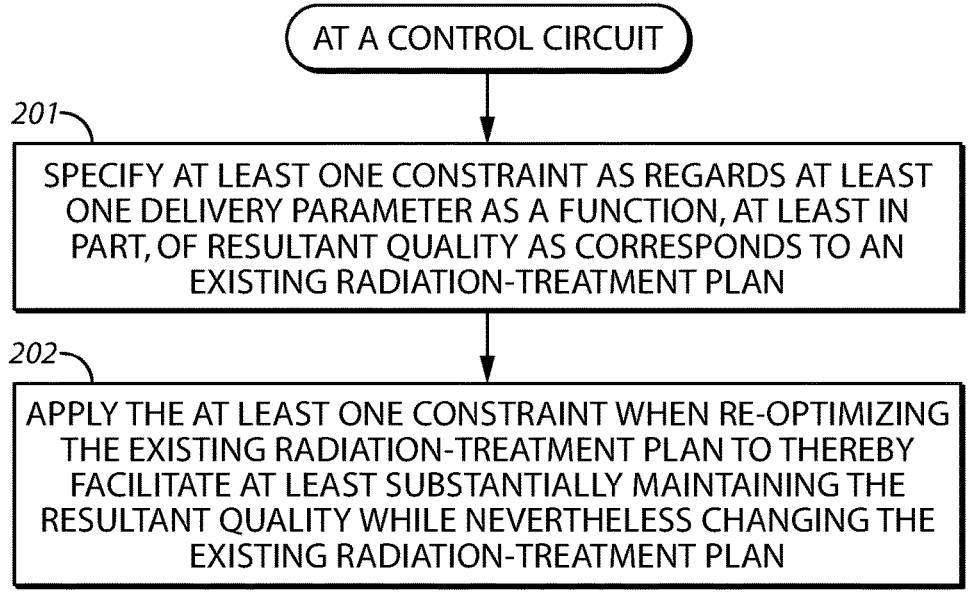
FIG. 2 comprises a flow diagram as configured in accordance with various embodiments of the invention.

Referring now to FIG. 2, another illustrative process 200 that is compatible with many of these teachings will be presented. This process 200 relates to facilitating the re-optimization of an existing radiation-treatment plan that has a corresponding resultant quality and that is defined, at least in part, by at least one delivery parameter. This existing radiation-treatment plan can be the result of having used the process 100 described above or can be the result of any number of other treatment-plan development methodologies as desired. This process 200 can also be carried out by an appropriately configured control circuit as described below.

At step 201 this process 200 provides for specifying at least one constraint as regards the at least one delivery parameter as a function, at least in part, of the aforementioned resultant quality. This specification activity can comprise, for example, setting the at least one constraint to correspond to at least one setting as comprises a part of that existing radiation-treatment plan. In effect, this can comprise seeking to assure that the delivered dose is acceptably close to the calculated dose. The latter can be important because the dose calculated in the planning phase is used for evaluating the quality of the treatment overall. One example of a quality metric used in such comparisons is referred to as gamma evaluation where the acceptance criteria is typically 95 percent of points that are within 3 percent of the dose level and within a distance of 3.0 millimeters.

The aforementioned delivery parameter can vary with the needs and/or opportunities as tend to characterize a given application setting. By one approach, for example, the delivery parameter can pertain to fluence. Fluence, of course, represents radiative flux integrated over time and comprises a fundamental metric in dosimetry (i.e., the measurement and calculation of an absorbed dose of ionizing radiation in matter and tissue). In this case, the constraint as regards the delivery parameter can comprise a maximum or minimum fluence to be applied to a target, adjacent tissue, a specific organ, and so forth.

Figure 3:
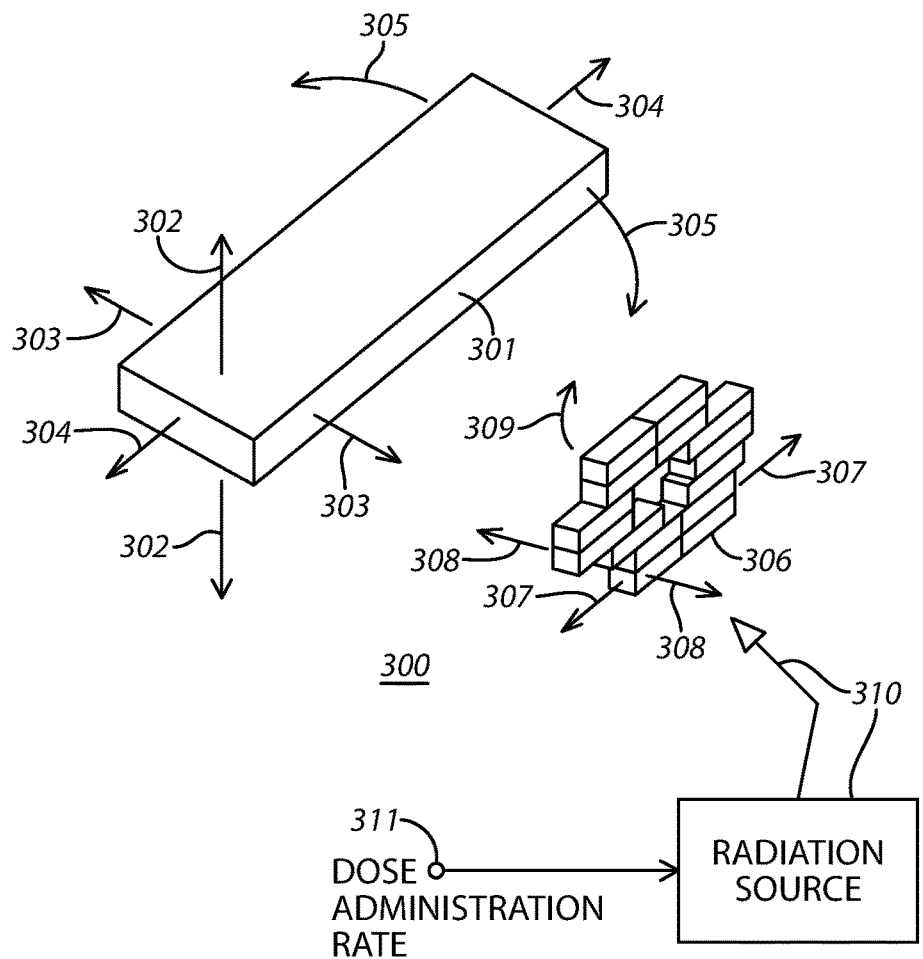
FIG. 3 comprises a perspective, schematic view as configured in accordance with various embodiments of the invention.

By another approach, in lieu of the foregoing or in combination therewith, the delivery parameter can pertain to some or all of the mechanical settings of a radiation-delivery apparatus. FIG. 3 illustrates some non-limiting examples in these regards. The mechanical setting or settings of interest can pertain, for example, to a patient support platform 301 (such as a couch). In such a case the mechanical setting can comprise, for example, vertical positioning 302 of the patient support platform 301, horizontal positioning 303 of the patient support platform 301, longitudinal positioning 304 of the patient support platform 301, and/or rotational positioning 304 of the patient support platform 301 at various times during the radiation-treatment session (such as, for example, during one or more delivery fractions). Other patient support platform positions can be accommodated as well as desired such as an angle of inclination of part or all of the patient support platform 301.

Other mechanical settings can pertain to one or more collimators as comprise a part of the radiation-delivery apparatus 300. A single multi-leaf collimator 306 serves as an illustrative example in these regards but it will be understood that other types and/or numbers of collimators can be readily accommodated in these same regards. In such a case, the mechanical setting(s) can comprise a collimator position (such as a side-to-side position 307 or an inward-or-outward position 308), a collimator angle 309, and/or one or more multi-leaf collimator leaf position settings. (Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. A radiation-treatment plan that presumes use of such a collimator will typically account for the position of each such leaf.)

And as yet another illustrative example in these regards, the mechanical setting can pertain to the specification location/orientation of one or more radiation sources 310 and/or the dose-administration rate 311. The dose-administration rate 311 can comprise, for example, the amount of energy over time that the apparatus 300 administers to the patient.

Referring again to FIG. 2, at step 202 this process 200 provides for applying the at least one constraint when re-optimizing the existing radiation-treatment plan to thereby facilitate at least substantially maintaining the resultant quality while nevertheless changing the existing radiation-treatment plan. By one approach, for example, this step 202 can comprise using that constraint to limit search space when re-optimizing the existing radiation-treatment plan. This might comprise, for example, limiting an allowed amount of change in fluence or multi-leaf collimator leaf movement. As another example for an optimization that can affect a gantry angle, collimator angle, or couch-rotation angle, this can comprise limiting changes to those rotation angles.

By another approach, in lieu of the foregoing or in combination therewith, this step 202 can comprise using the constraint to assess a distance between the existing radiation-treatment plan and at least one candidate re-optimized radiation-treatment plan. When, for example, that distance exceeds the specified constraint (either at all or in some suitably continuous and persistent manner as desired) the candidate re-optimized radiation-treatment plan can be discarded even if that re-optimized plan otherwise appears better than the existing plan in some other way or view.

Figure 4:
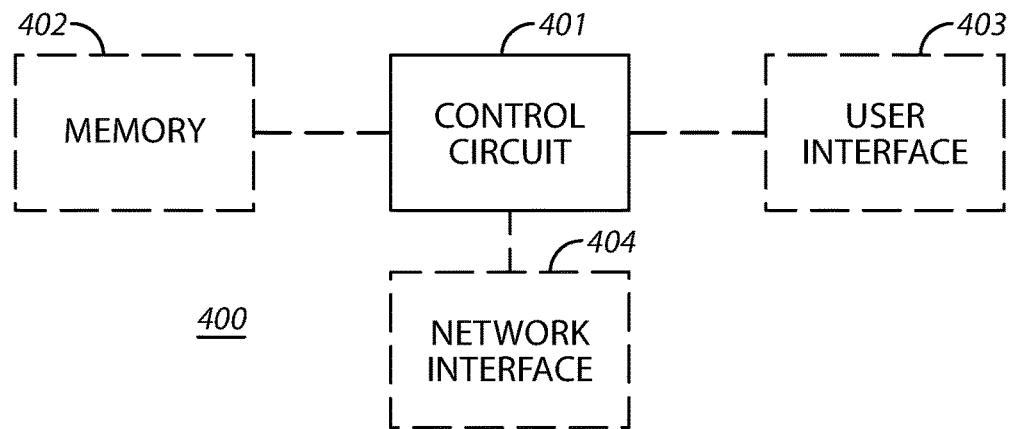
FIG. 4 comprises a block diagram as configured in accordance with various embodiments of the invention.

The above-described processes 100 and 200 are readily enabled using any of a wide variety of available and/or readily configured platforms, including partially or wholly-programmable platforms as are known in the art or dedicated-purpose platforms as may be desired for some applications. Referring now to FIG. 4, an illustrative approach to such a platform will now be provided.

In this illustrative the apparatus 400 comprises a control circuit 401. Such a control circuit 401 can comprise a fixed-purpose hard-wired platform or can comprise a partially or wholly-programmable platform. All of these architectural options are well known and understood in the art and require no further description here. This control circuit 401 is configured (for example, by using corresponding programming as will be well understood by those skilled in the art) to carry out one or more of the steps, actions, and/or functions described herein.

This control circuit 401 can operably couple to an optional memory 402 that may be integral to the control circuit 401 or can be physically discrete (in whole or in part) from the control circuit 401 as desired. This memory 402 can serve, for example, to non-transitorily store the computer instructions that, when executed by the control circuit 401, cause the control circuit 401 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

Depending upon the application setting this control circuit 401 can also operably couple to an optional user interface 403 and/or an optional network interface 404. The user interface 403 can comprise any of a variety of mechanisms to permit a user to enter data, selections, instructions, and so forth and/or to provide information to the user. Examples in these regards include, but are not limited to, keyboards and keypads, real and virtual buttons and switches, cursor control devices, displays of various kinds including touchscreen displays, voice-recognition components, printers, text-to-speech components, and so forth. The network interface 404, in turn, can comprise any of a variety of wireless and non-wireless interfaces to permit the control circuit 401 to access other resources via one or more intervening communication networks. These teachings are not particularly sensitive to any particular choices made in these regards; accordingly, further elaboration in these regards will not be provided here for the sake of brevity.

So configured, a radiation-treatment plan can be optimized and/or re-optimized in ways that achieve superior results in at least some application settings and/or that achieve satisfactory results using less time and/or computational resources. These teachings are useful for a wide variety of radiation-treatment modalities including numerous existing approaches.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method to facilitate optimizing a radiation-treatment plan comprised of a plurality of dose-delivery fractions, the method comprising:
by a control circuit:
optimizing the radiation-treatment plan using both fraction dose objectives and at least one other, different dose objective, wherein the other, different dose objective comprises, at least in part, a remaining total-dose objective and wherein using fraction dose objectives comprises, at least in part, accumulating doses delivered in previous dose-delivery fraction by, at least in part:
producing a mapping from fraction geometry to reference geometry by determining a deformable image registration between a patient image and a reference patient image; and
using the mapping to accumulate doses in the reference geometry.

2. The method of claim 1 wherein the fraction dose objectives comprise, at least in part, dose-volume histogram (DVH) objectives.

3. The method of claim 1 wherein the other, different dose objective further comprises, at least in part, a predictive-dose objective.

4. An apparatus to facilitate optimizing a radiation-treatment plan comprised of a plurality of dose-delivery fractions, the apparatus comprising:
a control circuit configured to optimize the radiation-treatment plan using both fraction dose objectives and at least one other, different dose objective, wherein the other, different dose objective comprises, at least in part, a remaining total-dose objective and wherein using fraction dose objectives comprises, at least in part, accumulating doses delivered in previous dose-delivery fraction by, at least in part:
producing a mapping from fraction geometry to reference geometry by determining a deformable image registration between a patient image and a reference patient image, and
using the mapping to accumulate doses in the reference geometry.

5. The apparatus of claim 4 wherein the fraction dose objectives comprise, at least in part, dose-volume histogram (DVH) objectives.

6. The apparatus of claim 4 wherein the other, different dose objective further comprises, at least in part, a predictive-dose objective.

* * * * *